(12) United States Patent
Houston et al.

(10) Patent No.: US 8,021,415 B2
(45) Date of Patent: *Sep. 20, 2011

(54) INSERT FOR A CONDUIT

(75) Inventors: John Graeme Houston, Perth (GB); Peter Arno Stonebridge, Perth (GB); John Bruce Cameron Dick, Blairgowrie (GB); Robert Gordon Hood, Tayside (GB); Allana Johnstone, Dunblane (GB); Christophe Emmanuel Sarran, Perth (GB); Craig McLeod Duff, Tayside (GB)

(73) Assignee: Tayside Flow Technologies Limited, Dundee (GB)

( * ) Notice: Subject to any disclaimer, the term of this patent is extended or adjusted under 35 U.S.C. 154(b) by 341 days.

This patent is subject to a terminal disclaimer.

(21) Appl. No.: 12/009,269

(22) Filed: Jan. 17, 2008

(65) Prior Publication Data

US 2008/0114448 A1    May 15, 2008

Related U.S. Application Data

(63) Continuation of application No. 10/301,257, filed on Nov. 21, 2002, now Pat. No. 7,331,989.

(30) Foreign Application Priority Data

Nov. 21, 2001 (GB) .................................. 0127888.6

(51) Int. Cl.
*A61F 2/06* (2006.01)
*A61F 2/82* (2006.01)
*F15D 1/02* (2006.01)

(52) U.S. Cl. ........... 623/1.22; 623/1.1; 138/39; 138/129

(58) Field of Classification Search .............. 606/108, 606/200; 623/1.22, 1.24, 1.26, 1.15, 1.32, 623/1.33, 900; 138/39, 129, 112, 172; 428/34.1, 428/35.7, 35.8, 36.9; 604/8

See application file for complete search history.

(56) References Cited

U.S. PATENT DOCUMENTS

| | | | |
|---|---|---|---|
| 2,831,662 A | 4/1958 | Hirsch | 165/156 |
| 4,161,966 A | 7/1979 | Scheffler et al. | 138/112 |
| 4,420,019 A | 12/1983 | Dillon | 138/129 |
| 4,553,545 A | 11/1985 | Maass et al. | 606/198 |
| 4,596,548 A | 6/1986 | DeVries et al. | 604/4 |
| 4,629,458 A | 12/1986 | Pinchuk | 623/1 |
| 4,747,697 A * | 5/1988 | Kojima | 366/339 |
| 4,760,849 A | 8/1988 | Kropf | 606/191 |
| 5,129,910 A * | 7/1992 | Phan et al. | 606/127 |
| 5,416,270 A | 5/1995 | Kanao | 174/47 |
| 5,486,191 A | 1/1996 | Pasricha et al. | 606/191 |
| 5,500,013 A | 3/1996 | Buscemi et al. | 623/1.22 |

(Continued)

FOREIGN PATENT DOCUMENTS

DE          597 472 C       1/1936

(Continued)

OTHER PUBLICATIONS

Translation of WO 98/58599, Dec. 1998, Stergiopulos.*

(Continued)

*Primary Examiner* — Elizabeth Houston
(74) *Attorney, Agent, or Firm* — Renner, Kenner, Greive, Bobak, Taylor & Weber

(57) ABSTRACT

There is disclosed an insert (2) for a conduit (4) adapted to effect helical flow in the conduit (4) comprising a longitudinally extending member having a helical formation.

19 Claims, 4 Drawing Sheets

U.S. PATENT DOCUMENTS

| | | | | |
|---|---|---|---|---|
| 5,653,745 A | * | 8/1997 | Trescony et al. | 623/1.29 |
| 5,669,420 A | | 9/1997 | Herrero et al. | 138/135 |
| 5,718,973 A | | 2/1998 | Lewis et al. | 623/1.32 |
| 5,776,160 A | | 7/1998 | Pasricha et al. | 606/191 |
| 5,924,456 A | | 7/1999 | Simon | 138/122 |
| 5,992,465 A | * | 11/1999 | Jansen | 138/37 |
| 6,019,779 A | | 2/2000 | Thorud et al. | 606/198 |
| 6,063,111 A | * | 5/2000 | Hieshima et al. | 623/1.22 |
| 6,071,305 A | * | 6/2000 | Brown et al. | 623/1.43 |
| 6,156,062 A | | 12/2000 | McGuinness | 623/1.22 |
| 6,161,399 A | | 12/2000 | Jayaraman | 66/170 |
| 6,190,402 B1 | | 2/2001 | Horton et al. | 623/1 |
| 6,364,904 B1 | | 4/2002 | Smith | 623/1.22 |
| 6,416,540 B1 | | 7/2002 | Mathur | 623/1.15 |
| 6,572,648 B1 | | 6/2003 | Klumb et al. | 623/1.15 |
| 6,641,605 B1 | * | 11/2003 | Stergiopulos | 623/1.1 |
| 6,645,237 B2 | | 11/2003 | Klumb et al. | 623/1.11 |
| 6,660,032 B2 | | 12/2003 | Klumb et al. | 623/1.13 |
| 6,675,901 B2 | | 1/2004 | Johnson et al. | 166/380 |
| 6,776,194 B2 | | 8/2004 | Houston et al. | 138/39 |
| 6,921,414 B2 | | 7/2005 | Klumb et al. | 623/1.15 |
| 7,185,677 B2 | | 3/2007 | Houston et al. | 138/39 |
| 7,331,989 B2 | | 2/2008 | Houston et al. | 623/1.22 |
| 2001/0000794 A1 | | 5/2001 | Daubert et al. | 604/200 |
| 2001/0027341 A1 | | 10/2001 | Gianotti | 623/1.22 |
| 2001/0027693 A1 | | 10/2001 | Blaurock | 74/424.75 |
| 2001/0053931 A1 | | 12/2001 | Hess et al. | 623/1.15 |
| 2002/0179166 A1 | | 12/2002 | Houston et al. | 138/39 |
| 2003/0225453 A1 | | 12/2003 | Murch | 623/1.21 |
| 2004/0037986 A1 | | 2/2004 | Houston et al. | 428/36.9 |
| 2006/0124187 A1 | | 6/2006 | Houston et al. | 138/39 |

FOREIGN PATENT DOCUMENTS

| | | |
|---|---|---|
| DE | 25 10 169 A1 | 9/1976 |
| EP | 0 077 130 A1 | 4/1983 |
| EP | 0 405 303 A1 | 6/1990 |
| EP | 1 159 933 A2 | 12/2001 |
| FR | 2 655 548 | 6/1991 |
| WO | WO 90/04982 | 5/1990 |
| WO | WO 98/58599 * | 12/1998 |
| WO | WO 00/38591 | 7/2000 |
| WO | WO 01/89419 | 11/2001 |

OTHER PUBLICATIONS

WPI Abstract Acc. No. 1986-160610 of EPODOC abstract of NL8403279 A (Philips).

WPI Abstract Acc. No. 1991-258271 of SU1613835 A (ADAMOVSIJ).

* cited by examiner

INSERT FOR A CONDUIT

CROSS REFERENCE TO RELATED APPLICATION

This application is a continuation of U.S. patent Ser. No. 10/301,257, filed Nov. 21, 2002 now U.S. Pat. No. 7,331,989, which is incorporated herein by reference.

FIELD OF THE INVENTION

This invention relates to an insert for a conduit, and especially, but not solely, an insert to modify flow in blood flow tubing such as veins and arteries of the human or animal body for the purpose of effecting helical flow therein.

DESCRIPTION OF THE PRIOR ART

WO 00/38591 discloses modified blood flow tubing and stents for use in blood flow tubing with spiral configurations that induce spiral (or helical) flow in the tubing. There is evidence that spiral flow has a beneficial effect in reducing turbulence and dead flow spots in the tubing. It is believed that turbulence and dead flow spots contribute to the build up of plaque, or narrowing of blood vessels, which can result in blockage at or downstream of the tubing or stent.

Stents are commonly used to open up and/or maintain open constricted arteries, and, as disclosed in WO 00/38591, can incorporate helical formations to induce the desired spiral flow.

However, stents are already of some complexity, arising from the need to introduce them in compact form for easy passage through the artery to the target site, then to expand them to open the restriction or to fit a previously opened restriction. Introducing a helical flow inducing configuration is an added complication.

SUMMARY OF THE INVENTION

In accordance with a first aspect of the present invention, there is provided an insert for a conduit, the insert being adapted to effect helical flow in the conduit and comprising a longitudinally extending member defining at least a portion of a helix.

The terms "helix", "helical" and "spiral" as used herein cover the mathematical definition of helix and helical and any combination of the mathematical definitions of helical and spiral.

The longitudinally extending member may be, in cross-section, flat. However, it may have an inwardly extending portion that extends inwardly of the helix and also extends lengthwise along the member. The inwardly extending portion may extend along an edge of the longitudinally extending member, or may extend, lengthwise, intermediate the edges of the longitudinally extending member.

The longitudinally extending member may have two inwardly extending portions, and preferably, at least one may extend lengthwise along an edge of the longitudinally extending member.

Preferably, the inwardly extending portion, or portions, is movable between the inwardly extended position and a collapsed position. This has the advantage that where the insert is used in a stent, the portion(s) can be moved to the collapsed position when the stent is collapsed to facilitate insertion of the stent. Typically, the inwardly extending portion, or portions, are biased towards the extended position. Hence, when the stent is expanded, the inwardly extending portion(s) move when permitted to the extended position. Preferably, the biasing of the inwardly extending portions to the extended position is enabled by an elastic deformation of the inwardly extending portion(s) to the collapsed position(s). For example, the inwardly extending portion may be elastically compressible or elastically deflectable to the collapsed position.

Typically, the longitudinally extending member is adapted to be attached to an internal side wall of a conduit, such as a stent, stent graft, or graft. In this example the longitudinally extending member defines a helix or helix/spiral combination around the longitudinal axis of the conduit.

Alternatively, it is possible that the longitudinally extending member may be so configured in relation to a conduit for which it is adapted that its cross-section at any position along the conduit is substantially on a diameter of the conduit cross-section.

The insert may be adapted to lodge inside a vein or artery of the human or animal body, and may be adapted to lodge inside a stent in a vein or artery of the human or animal body, or a graft therein.

The insert may have a pitch, in relation to its length, such that one end is angularly displaced from the other by less that one revolution. Typically, the revolution of the total length of the insert is at least 50%, and preferably at least 70% of one revolution. If multiple inserts are provided in the conduit, the revolution may be the combined total of the revolution of each insert.

Preferably, where the insert is for use in the human or animal body, the insert comprises a biocompatible material, if it is to be left for any length of time.

In one example of the invention, the insert may also be biodegradable, so that it can serve for a predetermined period of time without needing to be removed.

In accordance with a second aspect of the present invention, there is provided a stent comprising a tubular body member and an insert mounted within the body member, the insert comprising a longitudinally extending member defining at least a portion of a helix.

Preferably, the tubular body member is movable between a collapsed position, during insertion of the stent, and an expanded position, when the stent is located in the desired position.

Typically, the longitudinally extending member has an inwardly extending portion that extends inwardly away from the internal side-walls of the tubular body section. Preferably, the inwardly extending portion is movable to a collapsed position.

In one example of the invention, the stent comprises a single insert. However, in other examples of the invention, the stent may comprise two or more inserts, typically, on the same cross-section of the tubular body member.

Typically, the portion of a helix defined by the longitudinally extending member is at least 50% of one revolution, and preferably at least 70% of one revolution. However, if multiple inserts are provided, the total portion of a helix defined by all the longitudinally extending members may be at least 50%, and preferably, at least 70% of one revolution.

Preferably, the insert has two inwardly extending portions extending along the length of the longitudinally extending member. However, alternatively, the insert may have only one inwardly extending portion extending along the length of the longitudinally extending member.

BRIEF DESCRIPTION OF THE DRAWINGS

Inserts for a conduit in accordance with the invention will now be described with reference to the accompanying drawings, in which.

DETAILED DESCRIPTION OF THE PREFERRED EMBODIMENTS

Figure 1:
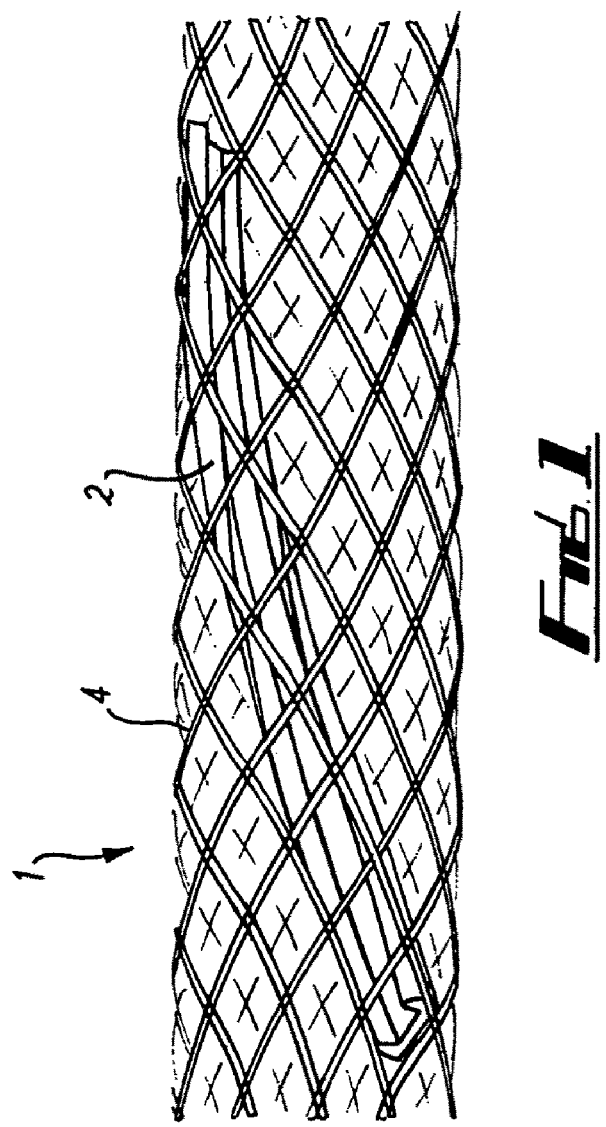
FIG. 1 is a side view of a stent with a first insert.
Figure 2:
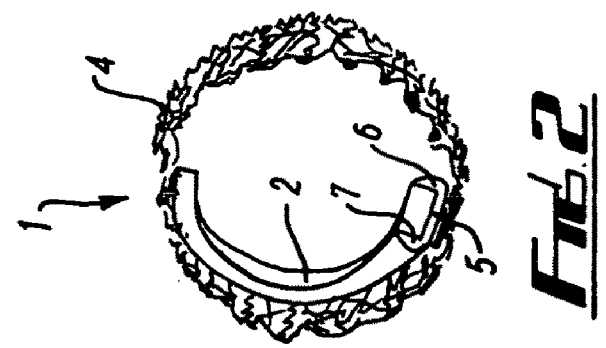
FIG. 2 is an end view of the stent of FIG. 1.

FIGS. 1 and 2 show a stent 1 having a main body 4 which is formed from a wire mesh material. Alternatively, the stent 1 could be formed from a tube with interruptions or a laser cut tube providing an expandable homogeneous structure. Attached to the internal side wall of the body 4 is an insert 2 which defines a helix. The insert 2 is typically manufactured from a biocompatible material, such as polyurethane, and may be attached to the internal side wall of the body 4 by injection moulding, insert moulding, glue or melting base portion 5 of the insert 2 onto the body 4 such that after cooling, the mesh structure of the body 4 is entrained with the base portion 5 of the insert 2.

Figure 3:
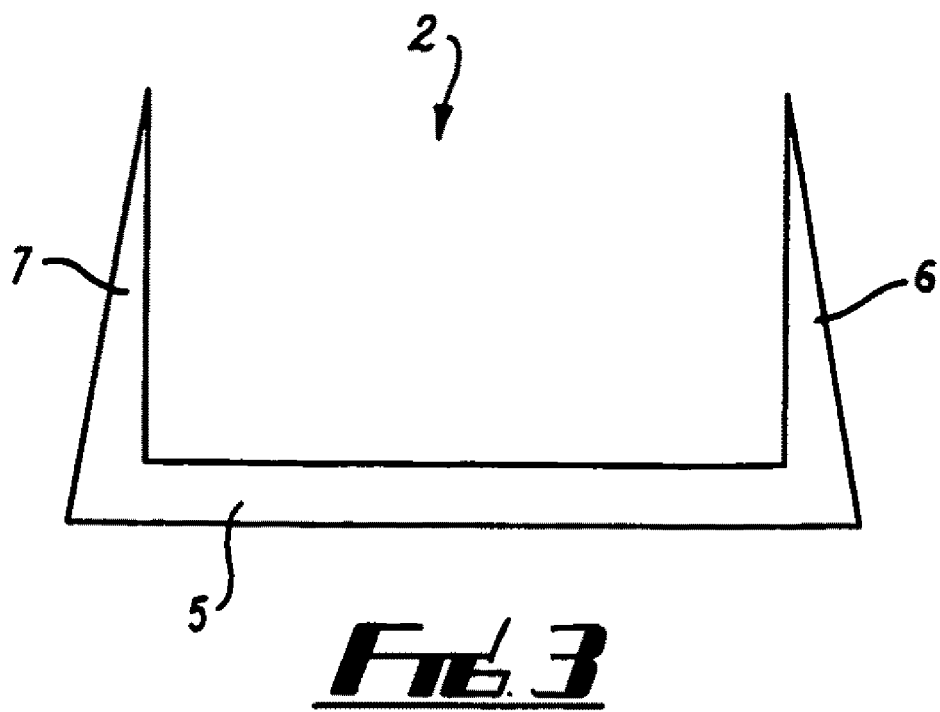
FIG. 3 is a cross-section view of the first insert in an open position.

A cross-sectional view of the insert 2 is shown in FIG. 3 where it can be seen that insert 2 also includes two fins 6, 7 extending from the base portion 5 at opposite edges of the base portion 5. It will be noted from FIGS. 1 and 2 that the fins 6, 7 extend along the length of the insert 2 and extend inwardly from the internal side walls of the main body 4.

In use, the stent 1 is inserted into a blood vessel in the human or animal body in a collapsed configuration and after it is located in the correct position, it is expanded to engage with the side walls of the blood vessel to locate the stent 1 in the desired position. Typically, the stent 1 is inserted on a balloon catheter with the stent 1 in the collapsed configuration around the collapsed balloon of the catheter. When the stent 1 is in the correct position in a blood vessel, the balloon is then inflated by pumping fluid into the balloon through the catheter. The expansion of the balloon expands the stent 1 into engagement with the internal side walls of the blood vessel. The configuration of the stent 1 shown in FIG. 1 is in the expanded position. That is, the configuration after it is engaged with the internal side walls of the vessels by expanding the balloon of a balloon catheter, and the balloon catheter is removed.

Alternatively, the stent 1 may be formed from an expansible material that "self-expands" into position, for example, by thermal mending properties.

Figure 4:
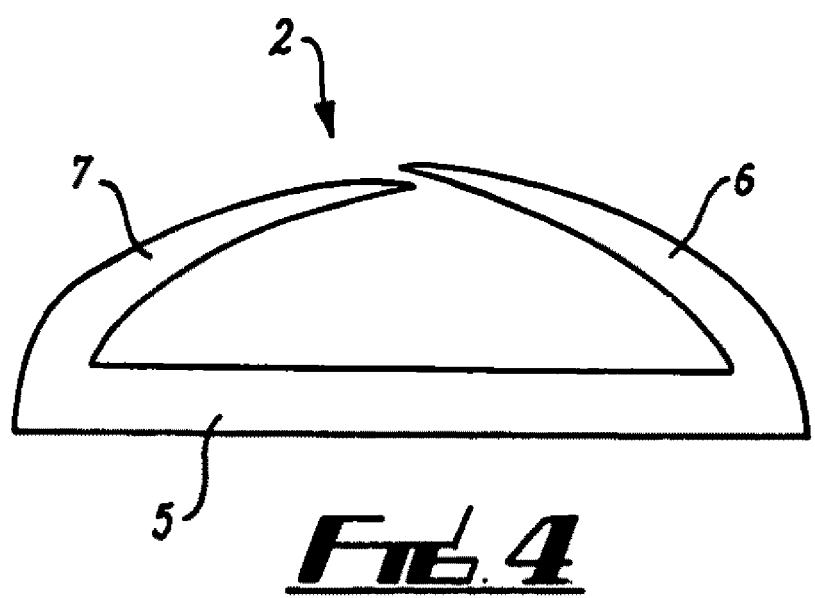
FIG. 4 is a cross-section view of the first insert in a collapsed position.

When the stent 1 is collapsed onto the balloon of the catheter, or the stent delivery system, the insert 2 is designed such that the fins 6, 7 are bent inwardly so that the fins of the insert collapse so as to reduce the volume occupied by the insert 2 when the stent 1 is in the collapsed configuration. This is illustrated in FIG. 4 where it can be seen that fin 7 bends inwardly to overlie the base 5 and fin 6 bends inwardly to overlie the fin 7. This feature is enabled by appropriate design of the base portion 5 and fins 6, 7 and a suitable choice of material for the insert 2. Typically, this is an elastically deformable material, such as a suitable plastic material, for example, polyurethane. Hence, as the collapsing is an elastic deformation of the insert 2, the fins 6, 7 automatically return to the non-collapsed position, shown in FIG. 2, after expansion of the stent 1 and removal of the balloon catheter.

After insertion and placement in the desired blood vessel, the insert 2, due to its helical shape, acts on blood flowing through the stent 1 to generate a spiral flow component in the blood.

The length of the stent 1 is to a large extent dictated by enabling sufficient flexibility to ensure that the stent 1 can be inserted into the desired location in the human or animal body or the length of the narrowed artery requiring or able to be supported by the stent. That is, the length may depend on the length of the vessel needing treatment. Accordingly, the stent 1 typically has a length in the region of 10 mm to 100 mm. For certain vessels this may be normally approximately 20 mm to 40 mm in length. In order for the insert 2 to generate spiral flow of blood passing through the stent 1, the helix angle of the helix defined by the insert 2 must not be too high. Therefore, to generate an effective spiral flow component, the insert 2 typically defines only a portion of one revolution of the helix that it defines. Preferably, this is at least 50% of one revolution and most preferably greater than 70% of one revolution. However, the effect may be enhanced by using a number of inserts 2 within the stent 1.

When blood flows through the stent 1, the helical formation of the insert 2 will tend to generate a spiral flow formation in the blood exiting from the stent 1. This spiral flow tends to reduce turbulence and promote better flow of blood within the blood vessels of the human or animal body into which it is inserted.

Figure 9:
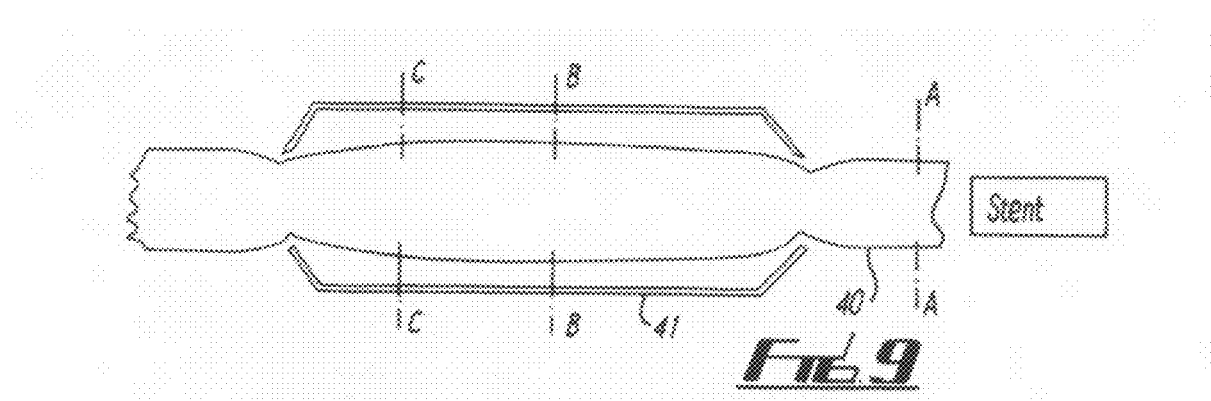
FIG. 9 is a schematic diagram showing relative positions of a cuff and a stent in a carotid artery of a pig.

This has been supported by experimental results. A pig had the stent 1 inserted, on a balloon catheter delivery system, in the left carotid artery and a cuff applied surgically to the artery downstream of the stent. A prior art stent identical to the stent 1, except for the absence of the insert 2, was inserted in a similar manner in the right carotid artery and a cuff was also applied surgically to the right carotid artery downstream of the prior art stent. The stent placements and the downstream cuffs were checked by intra-arterial contrast injection under X-ray (angiography). The cuffs 41 applied a moderate stenosis to each of the right and left carotid arteries 40 downstream of the stent. The cuffs 41 each produced a stenosis of approximately 75%. The relative positions of the stents in the carotid arteries 40 and the cuffs 41 are shown in FIG. 9.

Figure 10:
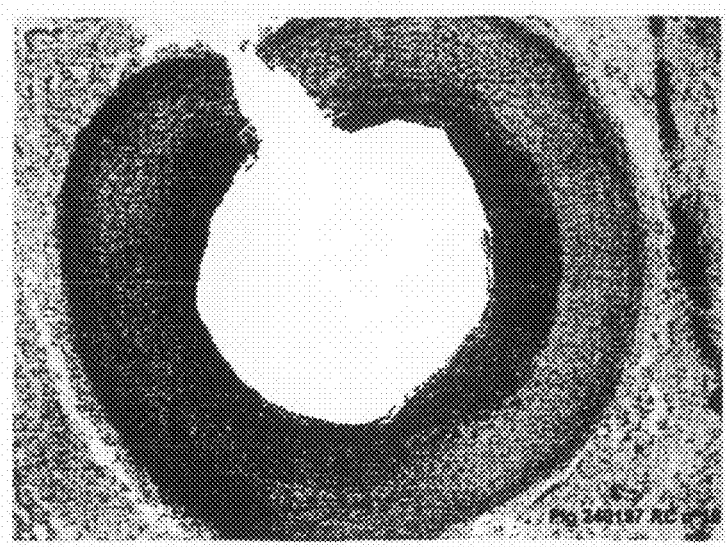
FIG. 10 is a section along the line CC of FIG. 9 of a right carotid artery fitted with a prior art stent.
Figure 11:
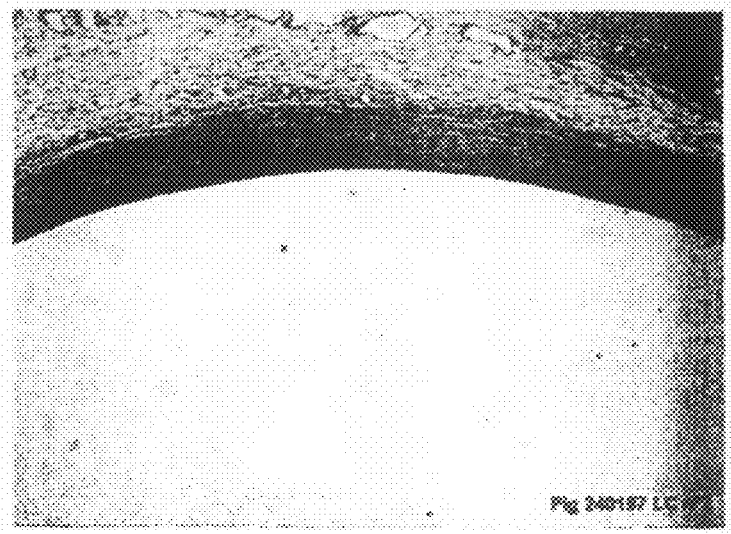
FIG. 11 is a section along the line CC of FIG. 9 of a left carotid artery of a pig fitted with the stent shown in FIGS. 1 and 2.

After two weeks the left and right carotid arteries 40 were explanted and examined grossly and histologically. The three sites along the carotid arteries 40 which were compared for the right and left carotid arteries 40 are indicated by the lines AA, BB and CC in FIG. 9. At each site AA, BB, CC the intimal and medial thickness and the intimal/medial thickness ratio were determined. The results are shown in Table 1 below and sections at site CC for the right and left carotid arteries are shown in FIGS. 10 and 11, respectively.

TABLE 1

| Pig Artery | Section | Intimal (µm) | Medial (µm) | I + M (µm) | I/M (%) |
|---|---|---|---|---|---|
| Left Carotid | AA | 35.6 | 649.8 | 685.4 | 5.5 |
|  | BB | 6.0 | 362.2 | 368.2 | 1.2 |
|  | CC | 5.7 | 250.4 | 240.7 | 2.7 |

TABLE 1-continued

| Pig Artery | Section | Intimal (μm) | Medial (μm) | I + M (μm) | I/M (%) |
|---|---|---|---|---|---|
| Right Carotid | AA | 48.7 | 680.8 | 729.6 | 7.2 |
| | BB | 52.5 | 628.7 | 681.1 | 8.4 |
| | CC | 347.3 | 387.5 | 734.9 | 89.7 |

A comparison of FIGS. 10 and 11 shows that there was extensive intimal thickening in the distal cuff of the right carotid artery (i.e. the artery with the prior art stent) but little intimal thickening in the distal cuff of the left carotid artery (i.e. the artery with the stent 1). This is supported quantitatively by Table 1, which shows that intimal/medial thickness ratio at location CC was 89.7% for the right carotid artery, but only 2.7% for the left carotid artery. In addition, it can be seen from FIG. 10 that there was also loss of lumen of the right artery at site CC. While FIG. 11 shows that there was no loss of lumen of the left artery at site CC.

As an alternative to attaching the insert 2 directly to the body 4, it is also possible that the insert 2 may be attached to a flexible material, such as a membrane, and that the flexible material is then attached to the inside and/or outside of the body 4. For example, the flexible material may be a woven, knitted or spun polyester material, polyurethane material or extended PTFE material, and may be in the form of a tube which locates within the body 4 and is attached to the body 4 by a suitable means, such as adhesive or by stitching. The flexible material may be porous.

Although in the stent 1 only one insert 2 is used, it is possible that multiple inserts may be used in either end-to-end and/or side-by-side relationship within the body 4. Where multiple inserts are used, the total portion of the helix defined by all the inserts is typically greater than 50% and preferably greater than 70%. This means that any one insert may define a portion of a helix that is less than 50%.

Figure 5:
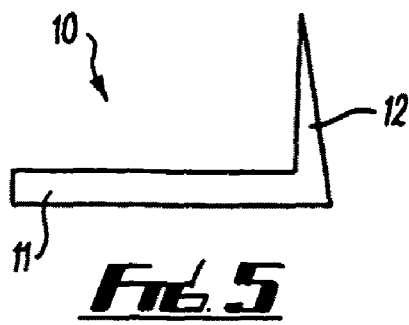
FIG. 5 is a cross-sectional view of a second insert.

FIG. 5 shows a second example of an insert 10 that includes a base portion 11 with a fin 12 extending from one edge of the base portion 11. As with the insert 2, the fin 12 extends along the length of the insert 10.

Figure 6:
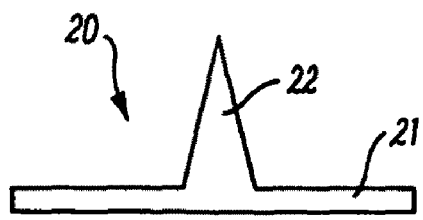
FIG. 6 is a cross-sectional view of a third insert.

FIG. 6 shows a third example of an insert 20 that includes a base portion 21 with a fin 22 extending centrally from the base portion 21. As with the inserts 2, 10 the fin 22 extends along the length of the insert 20.

Figure 7:
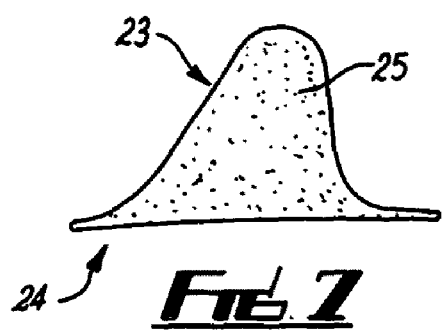
FIG. 7 is a cross-sectional view of a fourth insert in an extended position.
Figure 8:
FIG. 8 is a cross-sectional view of the fourth insert in a collapsed position.

FIGS. 7 and 8 show a fourth example of an insert 24 that has a fin 23 formed from an elastically compressible foam material 25, such as a polyurethane foam. FIG. 7 shows the insert 24 with the fin 23 in the extended position and FIG. 8 shows the insert 24 with the foam material 25 compressed so that the fin 23 is collapsed.

The inserts 10, 20, 24 may be used in the stent 1 in the same manner as the insert 2.

The helical formations 2, 10, 20, 24 may each have a pitch, in relation to their length, such that one end is angularly displaced from the other by at least 50% of one revolution and preferably at least 70% of one revolution. This is found to impart favourable spiral flow to flow in a vein or artery, eliminating, or at least reducing, turbulence and dead spots with reduction of plaque formation.

For helical formations 2, 10, 20, 24 intended to remain on more than just a temporary basis, a biocompatible material will be selected, and a smooth structure with rounded ends will be preferred so as not to introduce any turbulence into the flow.

The use of stents as described is clearly not restricted to blood flow tubing. Other tubing—including external blood flow, eg. dialysis and heart-lung machine tubing, as well as tubing and pipework in industrial and civil engineering could also benefit from inserts, as described herein, and the invention, whilst it has been specifically described and illustrated with reference to blood flow tubing is to be regarded as of more general application.

We claim:

1. An insert for a conduit comprising a longitudinally extending member comprising a base portion and at least one inwardly extending portion wherein the base portion and the at least one inwardly extending portion define at least a partial helix about the longitudinal axis of the conduit consisting of at least 50% of one revolution and wherein the at least one inwardly extending portion extends radially inwardly from the base portion and is laterally bendable relative to the base portion in the plane perpendicular to the longitudinal axis of the conduit from a collapsed position to an inwardly extended position wherein the inwardly extending portion overlies the base portion in the collapsed configuration.

2. The insert of claim 1, wherein said at least one inwardly extending portion extends along an edge of the base portion.

3. The insert of claim 1, wherein said at least one inwardly extending portion extends lengthwise and intermediate the edges of the base portion.

4. The insert of claim 1, wherein said longitudinally extending member has a plurality of inwardly extending portions.

5. The insert of claim 4, wherein said inwardly extending portions are connected by the base portion.

6. The insert of claim 1, wherein said insert is adapted to lodge inside a vein or artery of the human or animal body, or a graft therein.

7. The insert of claim 1, wherein said insert is adapted to lodge inside a stent in a vein or artery of the human or animal body, or a graft therein.

8. The insert of claim 1 wherein said partial helix consists of less than one revolution.

9. The insert of claim 1, wherein said partial helix consists of at least 70% of one revolution but less than one revolution.

10. The insert of claim 1, wherein said insert is manufactured from a material comprising a biocompatible material.

11. The insert of claim 1, wherein said insert is manufactured from a material comprising a biodegradable material.

12. A stent comprising a tubular body section defining an inside surface of the stent and an insert mounted on the inside surface, the insert comprising a longitudinally extending member comprising a base portion and at least one inwardly extending portion wherein the base portion and the at least one inwardly extending portion define at least a partial helix about the longitudinal axis of the tubular body section consisting of at least 50% of one revolution and wherein the at least one inwardly extending portion, extends radially inwardly from the base portion and is laterally bendable relative to the base portion in the plane perpendicular to the longitudinal axis of the tubular body section from a collapsed position to an inwardly extended position inwardly extending position wherein the inwardly extending portion overlies the base portion in the collapsed configuration.

13. The stent of claim 12, wherein the insert has a plurality of inwardly extending portions.

14. The stent of claim 13, wherein said inwardly extending portions are joined by the base portion.

15. The stent of claim 14, wherein said inwardly extending portions overlie said base portion in the collapsed position.

16. The stent of claim 12, wherein said longitudinally extending member comprises an elastically compressible material.

17. The stent of claim 12, wherein said partial helix consists of less than one revolution.

18. The stent of claim 12, wherein said partial helix consists of at least 70% of one revolution but less than one revolution.

19. The stent of claim 12, wherein the insert is mounted within a flexible tubular material and the flexible tubular material is mounted on the body section.

* * * * *